(12) United States Patent
Glen et al.

(10) Patent No.: US 12,350,117 B2
(45) Date of Patent: Jul. 8, 2025

(54) ORAL HYGIENE DEVICES CONFIGURED FOR USE WITH ORTHODONTICS

(71) Applicant: PerioNovum LLC, Bala Cynwyd, PA (US)

(72) Inventors: Jeffrey D. Glen, Bala Cynwyd, PA (US); Joshua C. Glen, Bala Cynwyd, PA (US)

(73) Assignee: PerioNovum LLC, Bala Cynwyd (PA)

( * ) Notice: Subject to any disclaimer, the term of this patent is extended or adjusted under 35 U.S.C. 154(b) by 751 days.

(21) Appl. No.: 17/448,809

(22) Filed: Sep. 24, 2021

(65) Prior Publication Data

US 2022/0087799 A1 Mar. 24, 2022

Related U.S. Application Data

(60) Provisional application No. 63/082,758, filed on Sep. 24, 2020.

(51) Int. Cl.
*A61C 17/02* (2006.01)
*A46B 9/04* (2006.01)
(Continued)

(52) U.S. Cl.
CPC .......... *A61C 17/0211* (2013.01); *A46B 9/045* (2013.01); *A46B 11/001* (2013.01); *A46B 15/0081* (2013.01); *A61C 19/063* (2013.01); *A61K 8/21* (2013.01); *A61Q 11/00* (2013.01); *A61K 2800/87* (2013.01); *A61K 2800/92* (2013.01)

(58) Field of Classification Search
CPC ... A46B 9/045; A46B 11/001; A46B 15/0081; A61C 19/063; A61C 17/0211; A61C 17/228; A61K 8/21; A61K 2800/87; A61K 2800/92; A61Q 11/00
USPC ........................................................ 15/167.2
See application file for complete search history.

(56) References Cited

U.S. PATENT DOCUMENTS

| | | | |
|---|---|---|---|
| 1,736,996 | A | 11/1929 | Dalmas |
| 3,769,652 | A | 11/1973 | Rainer |

(Continued)

FOREIGN PATENT DOCUMENTS

| | | |
|---|---|---|
| AU | 2015407320 B2 | 3/2017 |
| GB | 546136 A | 6/1942 |

(Continued)

OTHER PUBLICATIONS

International Search Report for International Application No. PCT/US2019/040197 dated Sep. 24, 2019.

(Continued)

*Primary Examiner* — Katina N. Henson
(74) *Attorney, Agent, or Firm* — Knobbe, Martens, Olson & Bear, LLC

(57) ABSTRACT

This application relates to oral hygiene and/teeth cleaning devices and associated methods configured for use with users having orthodontics such as braces. The devices can be configured to have a shape that allows all or substantially all of a user's teeth to be cleaned at once. In some embodiments, the devices are configured to be useable, for example, without access to water or a bathroom. The devices can be used to freshen up and clean the user's mouth on-the-go. In some embodiments, the devices are disposable.

19 Claims, 8 Drawing Sheets

(51) Int. Cl.
*A46B 11/00* (2006.01)
*A46B 15/00* (2006.01)
*A61C 19/06* (2006.01)
*A61K 8/21* (2006.01)
*A61Q 11/00* (2006.01)

(56) References Cited

U.S. PATENT DOCUMENTS

| | | | |
|---|---|---|---|
| 5,175,901 A * | 1/1993 | Rabinowitz | A46B 9/045 15/22.1 |
| 8,292,624 B2 * | 10/2012 | Gallagher, Jr. | A46B 11/0003 433/216 |
| 8,636,677 B2 | 1/2014 | Van Der Rijt | |
| 10,548,698 B2 * | 2/2020 | Fitzgerald | A61C 19/063 |
| 2004/0074035 A1 | 4/2004 | Huang | |
| 2008/0233541 A1 * | 9/2008 | De Vreese | A61C 19/066 433/216 |
| 2008/0280251 A1 | 11/2008 | Gallagher | |
| 2009/0208898 A1 * | 8/2009 | Kaplan | A46B 9/045 433/80 |
| 2009/0276972 A1 | 11/2009 | Dugan | |
| 2009/0277461 A1 | 11/2009 | Gallagher | |
| 2009/0320224 A1 | 12/2009 | Hohlbein | |
| 2010/0297197 A1 | 11/2010 | Golden | |
| 2012/0321369 A1 | 12/2012 | Herr et al. | |
| 2013/0067665 A1 * | 3/2013 | Sowinski | A46B 9/045 15/4 |
| 2014/0093836 A1 | 4/2014 | Wolpo | |
| 2014/0123421 A1 | 5/2014 | Fernandez | |
| 2014/0272761 A1 * | 9/2014 | Lowe | A61C 17/3481 433/2 |
| 2015/0282910 A1 | 10/2015 | Furdui-Carr | |
| 2016/0135581 A1 | 5/2016 | Pai | |
| 2016/0206415 A1 * | 7/2016 | Kraft | A61B 5/01 |
| 2016/0270892 A1 * | 9/2016 | Yoo | A61C 17/22 |
| 2017/0367801 A1 | 12/2017 | Fitzgerald | |
| 2018/0098832 A1 | 4/2018 | Pierce | |
| 2018/0228832 A1 * | 8/2018 | Hibi | A61K 31/727 |
| 2018/0368957 A1 | 12/2018 | Hyun | |
| 2019/0183619 A1 | 6/2019 | Reizenson | |
| 2020/0253703 A1 | 8/2020 | Ouin | |
| 2021/0161287 A1 | 6/2021 | Cadot | |

FOREIGN PATENT DOCUMENTS

| | | |
|---|---|---|
| WO | WO 2009/157932 A1 | 12/2009 |
| WO | WO 2015/024023 A1 | 2/2015 |
| WO | WO 2015/072676 | 5/2015 |
| WO | WO 2016/115276 A1 | 7/2016 |
| WO | WO-2020017963 A2 * | 1/2020 ............. A46B 13/06 |

OTHER PUBLICATIONS

Translation of Yoo document (Year: 2015).
"Is Swallowing Toothpaste Dangerous?" Islington Dental Clinic, Islington Dental Clinic, Feb. 21, 2020, islingtondentlclinic.com/nes-Is+swallowing+toothpaste+dangerous%3F-2072.(Year: 2020).

* cited by examiner

ORAL HYGIENE DEVICES CONFIGURED FOR USE WITH ORTHODONTICS

PRIORITY APPLICATION

This application claims priority to U.S. Provisional Application No. 63/082,758, filed Sep. 24, 2020, which is incorporated by reference herein. Any and all applications for which a foreign or domestic priority claim is identified in the Application Data Sheet as filed with the present application are hereby incorporated by reference under 37 CFR 1.57. This application is also related to U.S. application Ser. No. 16/459,301, published as U.S. Pub. No. 2020/0000564, and U.S. application Ser. No. 17/448,842, entitled "DEVICES AND METHODS FOR ORAL HYGIENE," filed on Sep. 24, 2021, each of which is also incorporated herein by reference.

BACKGROUND

Field

This application relates to oral healthcare, and in particular, to devices and methods for maintaining oral hygiene, cleaning teeth, and/or freshening the mouth, especially for users having orthodontics, such as braces.

Description

Oral hygiene is important for many reasons, including, for example, preventing dental decay and gum disease, and keeping breath fresh. Generally, people brush, floss, and use mouthwash to keep their mouth and teeth clean. Orthodontics, such as braces, are commonly used to straighten a person's teeth. Commonly, people get braces as a child or teenager. It can be difficult to keep one's teeth clean with braces as the braces provide many nooks and crannies for trapping food and/or bacteria.

BRIEF DESCRIPTION OF THE DRAWINGS

The features of the present disclosure will become apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

Figure 1B:
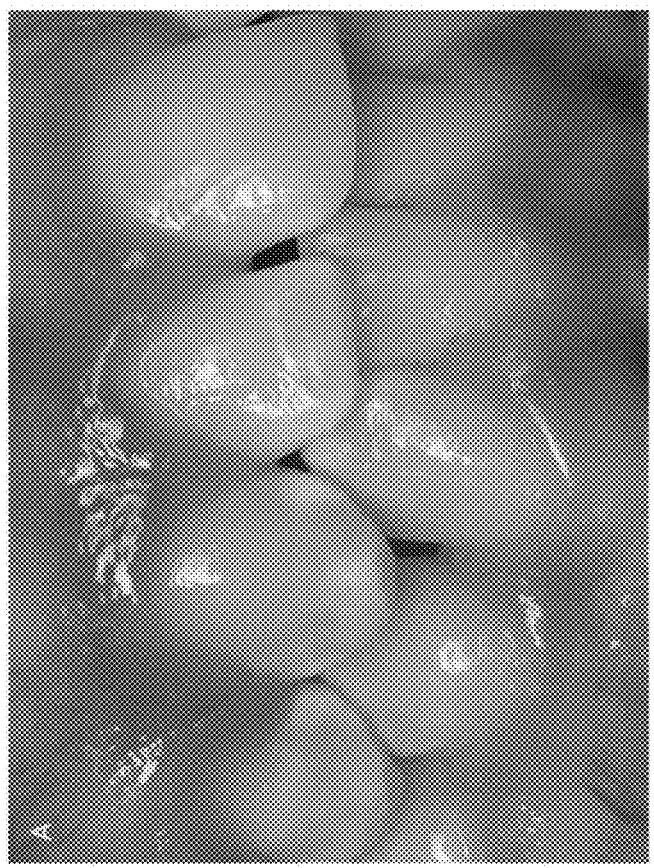
FIGS. 1A and 1B illustrate an example of white spot lesions (WSLs) on teeth including orthodontia, such as braces.

Various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

This application relates to oral hygiene and/or teeth cleaning devices and associated methods. In particular, the oral hygiene devices described herein can be configured for use with people having orthodontics, such as braces. The oral hygiene device can be specifically configured to clean around (e.g., above, below, or to the sides of) brackets which can be adhered to a person's teeth. Additionally, the devices can be configured to clean under the wires or other structures that extend between the brackets. Those who have had braces will appreciate that it is often challenging to clean one's teeth with braces. The braces provide many nooks and crannies that can collect food, bacteria, or other items that should be cleaned away. The oral hygiene devices described herein can be specifically configured to help to clean teeth that include orthodontics.

In some embodiments, the oral hygiene devices can be configured to have a shape that allows all or substantially all of a user's teeth (for example, all or substantially all of a user's upper teeth and/or all or substantially all of a user's lower teeth) to be cleaned at once. In some embodiments, the oral hygiene devices are configured to be useable, for example, without access to water or a bathroom. Thus, the oral hygiene devices can be used to freshen and clean the user's mouth and orthodontics while on-the-go. In some embodiments, the oral hygiene devices are disposable.

As noted previously, oral hygiene devices as described herein may be configured for use on patients having braces or other orthodontic treatment apparatus. In such cases, the ribs can be specially adapted to clean above and/or below the brackets of braces. Fixed orthodontic treatment presents many challenges to maintain optimal oral hygiene. Accumulation of plaque during treatment in, around, and above the brackets can lead to white spot lesions, gingival inflammation, and periodontal disease. Tooth brushing and home care is difficult and time-consuming for these ortho patients and generally, patient compliance is a significant issue. There should be a specific focus on teaching the patient how important it is to clean each individual bracket—especially between the bracket and gingival margin.

Figure 1A:
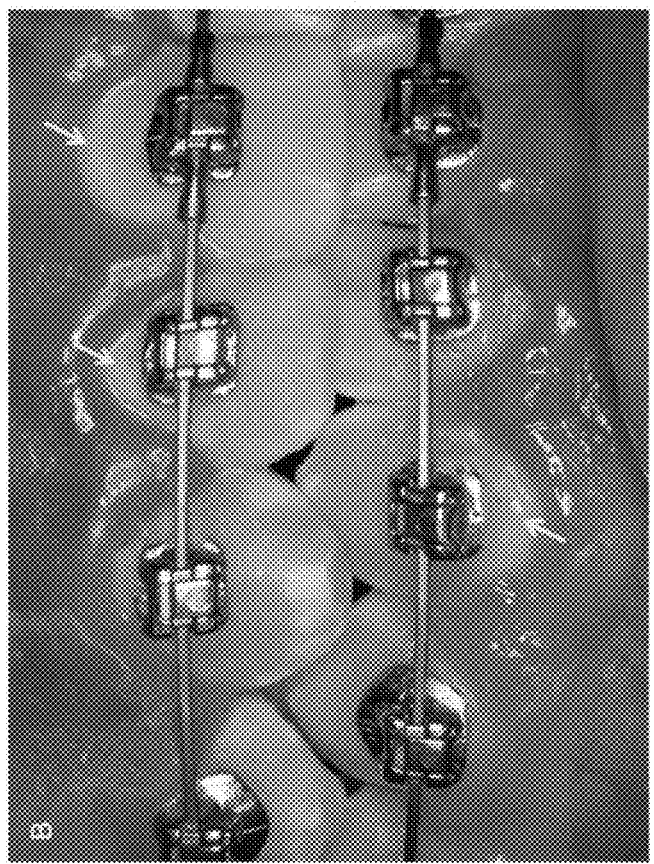

The most common adverse effects of this accumulation of plaque in this area are white spot lesions (WSL). WSL are enamel surface and sub-surface demineralization. Many times they appear within 1 month. Usually, these lesions are in sites adjacent to brackets on the buccal surface in the gingival region. Examples are shown in FIGS. 1A and 1B.

WSL are the precursor to decay. When orthodontic treatment is finished the white spots are permanent and lifelong. Other complications may develop. Patients may also often have gingival hypertrophy, gingival inflammation, bleeding, an increase in plaque, and calculus formation. Periodontal problems with aerobic and anaerobic bacteria can have even longer lasting and far-reaching consequences. Also, this biofilm formation can also weaken the bond strength of the adhesive, and brackets can fall off or compromise the end result.

Devices as described herein may be configured to address a major need in oral hygiene for consumers who have fixed orthodontic treatment. Mechanical removal of plaque especially above the bracket is essential for maintaining efficient hygiene. The features, aspects, and advantages of the present application will now be further described with reference to the drawings of several embodiments, which are intended to be within the scope of the embodiments disclosed herein. These and other embodiments will become readily apparent to those skilled in the art from the following detailed description of the embodiments having reference to the attached figures, the development not being limited to any particular embodiment herein disclosed.

Figure 2A:
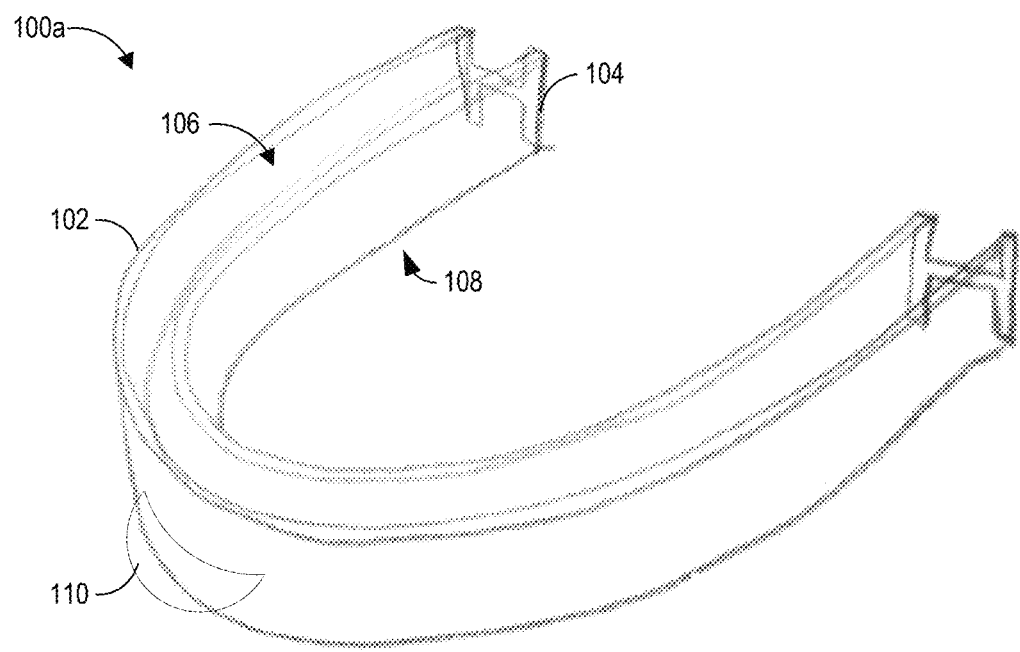
FIG. 2A is a perspective view of an embodiment of an oral hygiene device that includes an H-shaped cross-section.

FIG. 2A is a perspective view of an embodiment of an oral hygiene device 100a. The oral hygiene device 100a can be useable to freshen a user's mouth and/or clean the user's teeth, and in particular for users that have orthodontics, such as braces. The oral hygiene device 100a includes a body 102. In the illustrated embodiment, the body 102 is generally U-shaped (e.g., comprises a general U-shape when viewed from above or below). The generally U-shaped body 102 can be configured to follow or conform to the shape of a user's upper and/or lower teeth. In some embodiments, the body 102 may be a tray configured in size and shape to fit into the user's mouth and over the upper and/or lower teeth. The body 102 may be made of a rigid, semi-rigid, or flexible material, such as plastics or rubbers. In some embodiments, the body 102 comprises a thermoplastic elastomer (TPE), high-density polyethylene (HDPE), polypropylene (PP), low-density polyethylene (LDPE), polyamides, polyolefin or other resins, polychloro-trifluoroethylene, various thermoplastics, and/or various elastomers. In some embodiments, the body 102 may comprise a food grade polypropylene. The composition of the body 102 is not limited to the above materials, but can be selected for specific characteristics including enough rigidity to provide general support and shape for the oral hygiene device 100a, while also providing enough flexibility to allow the body 102 to fit to the particular anatomy of the user's mouth and teeth. In some embodiments, the oral hygiene device 100a can be provided in a variety of sizes (e.g., small, medium, large, adult, or child) configured for use by users that have different size mouths. In some embodiments, the oral hygiene device 100a can be provided in a size that is generally configured to fit most mouth sizes.

In the illustrated embodiment of FIG. 2A, the body 102 has a generally H-shaped cross-sectional profile 104. The generally H-shaped cross-sectional profile 104 can provide the body 102 with an upper channel 106 and a lower channel 108. The upper channel 106 can be configured to receive of be fitted over the user's upper teeth and associated orthodontia and the lower channel 108 can be configured to receive or be fitted over the user's lower teeth and associated orthodontia. For example, during use, the user may insert the oral hygiene device 100a into the mouth such that the upper teeth and orthodontia are positioned within the upper channel 106 and the lower teeth and orthodontia are positioned within the lower channel 108.

One or more of the inside surfaces of the upper channel 106 and the lower channel 108 may include features for cleaning the user's teeth (or otherwise freshening the user's mouth). For example, the inside surfaces of the upper channel 106 and the lower channel 108 can include bristles, foam, rubberized fingers, ribs, textured surfaces, etc., configured to clean the teeth when the oral hygiene device 100a is positioned within the mouth and moved back and forth and/or up and down. The teeth cleaning features are not shown in FIG. 2A, but examples will be shown and described below with reference to other embodiments. In particular, the teeth cleaning features can be specifically adapted to clean around orthodontia, such as braces, as described below.

In some embodiments, the teeth cleaning features within the upper channel 106 and the lower channel 108 are formed as part of the body 102. That is, in some embodiments, the teeth cleaning features can be integrally formed with the body 102. For example, the inside surfaces of the upper channel 106 and the lower channel 108 can be configured with a teeth cleaning texture that is molded into the body 102. In some embodiments, the teeth cleaning features can be made from the same material and/or formed at the same time as the body 102. For example, the body 102 and teeth cleaning features can be formed with a one-shot injection molding process in which a single material is injected into a mold to form the body 102 and teeth cleaning features simultaneously.

Advantageously, in some embodiments, the teeth cleaning features may comprise a different material than the body 102. For example, the teeth cleaning features may comprise a softer or more flexible material than the body 102. In such embodiments, the body 102 may be formed from a relatively stiffer or more rigid material in order to provide structural support for the device 100, and the teeth cleaning features can comprise a relatively more compliant or softer material in order to improve user comfort and cleaning efficiency. When made from different materials, the body 102 and the teeth cleaning features can be molded in a two-shot injection or overmolding process. For example, a first injection can be made using a first material to form the body 102, and then a second injection can be made using a second material to form the teeth cleaning features on the body 102.

The teeth cleaning features within the upper channel 106 and/or the lower channel 108 can be attached to the body 102 within the channels 106, 108. In the case of a two-shot injection or overmolding process, the teeth cleaning features are molded (and thereby connected) directly onto the body 102. In other embodiments, the body 102 and teeth cleaning features can be formed separately and then attached to each other, for example, with dental-grade adhesives.

In some embodiments, the upper channel 106 and the lower channel 108 can be lined with bristles, foam, rubberized fingers, ribs, etc., that are attached to the channels 106, 108. The shape, size, and combinations of the teeth cleaning features described herein are not limited to the above materials, but are selected for specific characteristics, including comfort to the mouth and gums and ability to clean teeth.

As illustrated in FIG. 2A, the oral hygiene device 100a includes a handle 110. In the illustrated embodiment, the handle 110 is positioned on a front portion of the body 102. The user can hold the handle while inserting the oral hygiene device 100a into the mouth and use the handle to manipulate the device (e.g., move the device up and down and/or back and forth) to use the device to clean his or her teeth. The handle 110 may be positioned and configured to extend out of the user's mouth between the user's lips when the oral hygiene device 100a is positioned within the mouth.

To use the oral hygiene device 100a, the user may use the handle 110 to insert the oral hygiene device 100a into his or her mouth. The user may position the oral hygiene device 100a such that the user's upper teeth are positioned within the upper channel 106 and the user's lower teeth are positioned within the lower channel 108. In this position, the upper and lower channels 106, 108 may contact the front, bottom, and back surfaces of the user's upper teeth and the front, top, and back surfaces of the user's lower teeth. Further, because of the generally U-shaped body the device 100a can contact all or substantially all of the user's upper and/or lower teeth. As used herein, "contacting substantially all of the user's upper and/or lower teeth" can refer to contact at least 50%, at least 60%, at least 70%, at least 80%, or at least 90% of the user's upper and/or lower teeth.

With the oral hygiene device 100a positioned within the mouth, the handle 110 may extend out of the user's mouth between the user's lips. Using the handle 110, the user may manipulate the oral hygiene device 100a by moving the handle 110 back and forth (e.g., side to side or right and left) and/or up and down. Manipulating the oral hygiene device 100a in this manner causes the teeth cleaning features within the upper channel 106 and the lower channel 108 to clean the teeth. After the user has used the device 100a to clean the teeth, which can be done for an indicated period of time, for example, 10 seconds, 15 seconds, 20 seconds, 30 seconds, 1 minute, 1.5 minutes, or 2 minutes, the user can remove the oral hygiene device 100a from the mouth. In some embodiments, the oral hygiene device 100a is disposable, and can then be discarded.

Notably, in some embodiments, the oral hygiene device 100a can be configured for use without requiring water. As such, the oral hygiene device 100a can be used generally anywhere to quickly clean and/or freshen up the user's mouth, without requiring the user to access a bathroom or running water. To this end, the oral hygiene device 100a can include dabs of mouthwash, breath freshener, toothpaste, desensitizing paste or gel as described below. In some embodiments, the dabs can be configured for use without requiring additional water. In some embodiments, the oral hygiene device 100a is configured for a single use. For example, the user may use the oral hygiene device 100a one time and then discard the device. In some embodiments, because the U-shaped body 102 covers many, and in some embodiments, all or substantially all of the user's teeth, the oral hygiene device 100a may be able to clean all or substantially all of the user's teeth much quicker than a toothbrush, which generally only contacts a few (e.g., one, two, or three) teeth at a time and must be moved over all the teeth in order to clean the whole mouth.

Figure 2B:
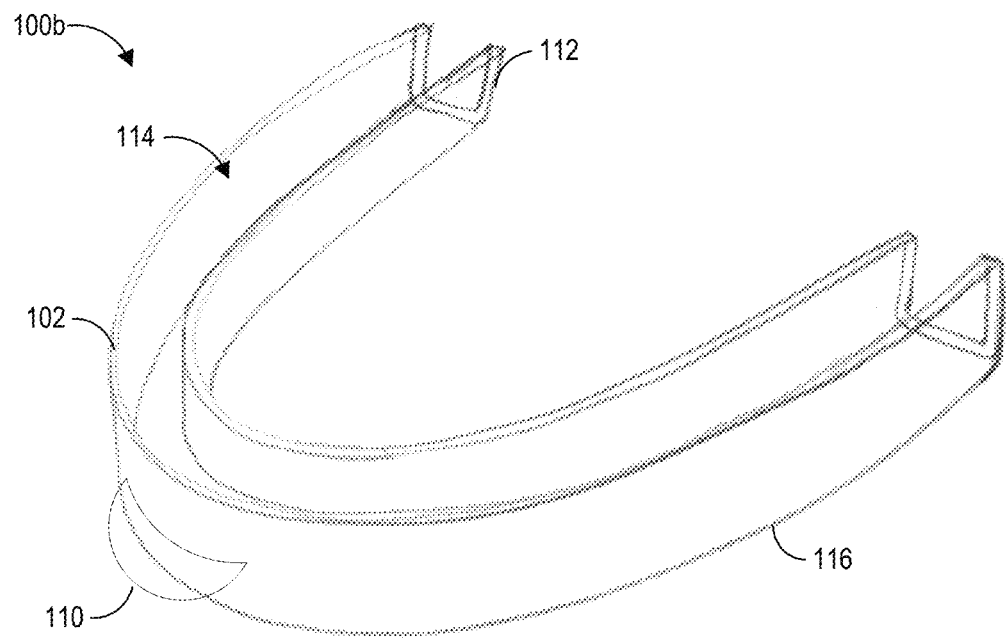
FIG. 2B is a perspective view of an embodiment of an oral hygiene device that includes a U-shaped cross-section.

FIG. 2B is a perspective view of another embodiment of an oral hygiene device 100b. The oral hygiene device 100b is similar in many respects to the oral hygiene device 100a described above with reference to FIG. 2A. However, as shown in FIG. 2B, the oral hygiene device 100b includes a body 102 with a generally U-shaped cross-sectional profile 112 (instead of the H-shaped cross-section 104 of FIG. 2A). The generally U-shaped cross-sectional profile 112 can provide a single channel 114 in the body 102 of the oral hygiene device 100b (in contrast with the upper and lower channels 106, 108 of the oral hygiene device 100a of FIG. 2A).

Similar to the description above, one or more of the inside surfaces of the channel 114 may include features for cleaning the user's teeth and orthodontia. For example, the inside surfaces of the channel 114 can include bristles, foam, rubberized fingers, ribs, textured surfaces, etc., configured to clean the teeth when the oral hygiene device 100b is positioned within the mouth and moved back and forth and/or up and down. As described above, the teeth cleaning features can be formed as part of the body 102, molded onto the body in a two-shot injection or overmolding process, or attached to the body 102 within the channel 114 and can be made of the same or different materials than the body 102.

With the generally U-shaped cross-sectional profile 114, the oral hygiene device 100b can be configured to clean either the user's upper teeth and associated orthodontia or the user's lower teeth and associated orthodontia at a time. In some instances, the device 100b can then be flipped over to clean the other of the user's upper teeth or the user's lower teeth. For example, the user may use insert the oral hygiene device 100b into the mouth such that the channel 114 is oriented in an upward direction and the user's upper teeth can be received within the channel 114. The user may then use the handle 110 to manipulate the device to allow the teeth cleaning features within the channel 114 to clean the user's upper teeth. The user may then remove the oral hygiene device 100b, flip the device over (such that the channel 114 opens in a downward direction), and reinsert the device such that the user's lower teeth are received within the channel 114. The user may again manipulate the device 100b such that the teeth cleaning features clean the user's lower teeth. Alternatively, the user may use the device 100b to clean the lower teeth first, followed by the upper teeth. In some instances, the user may use two of the devices 100b, one to clean the user's upper teeth and one to clean the user's lower teeth.

In some embodiments, the oral hygiene device 100b may include teeth or orthodontia cleaning features positioned on a side 116 of the body 102 opposite the channel 114. With reference to the illustrated orientation, the side 116 may be the lower or bottom side of the device. For example, in addition to including teeth cleaning features within the channel 114, the oral hygiene device 100b may also include teeth cleaning features (e.g., bristles, ribs, rubberized figures, foam, etc.) that extend from the lower side 116. Thus, in some embodiments, the oral hygiene device 100b (with its generally U-shaped cross-sectional profile 112) can be configured to clean both the upper and lower teeth of the user at the same time.

Figure 3A:
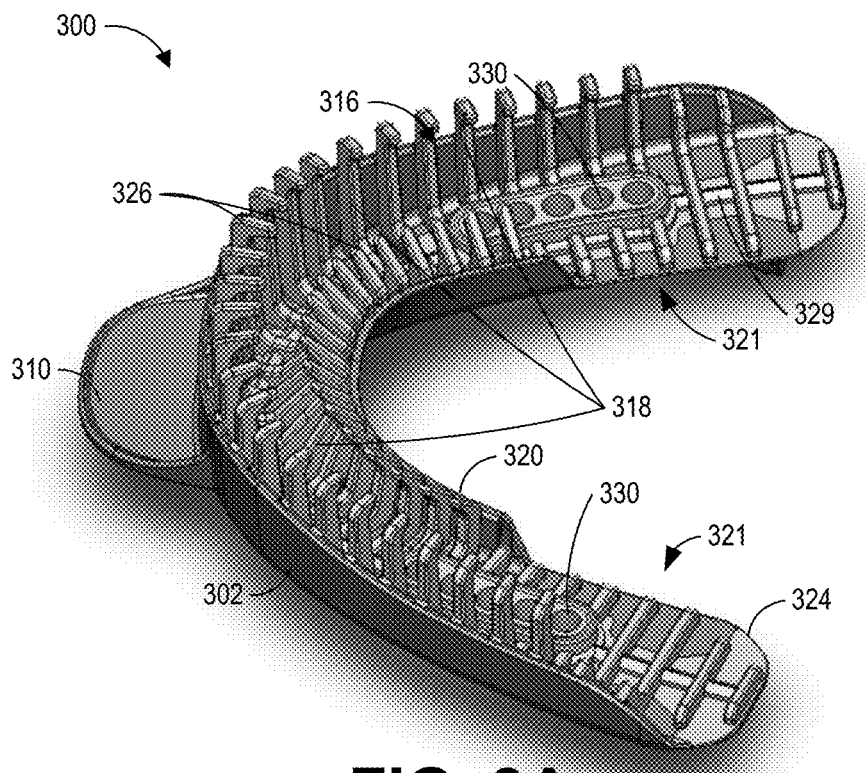
FIG. 3A is a top and side perspective view of another embodiment of an oral hygiene device.
Figure 3B:
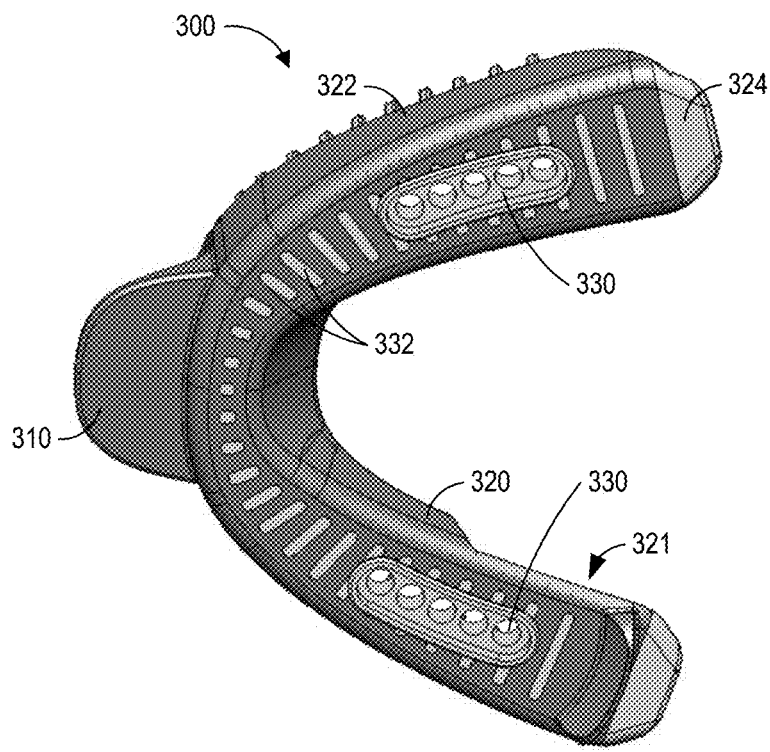
FIG. 3B is a bottom and side perspective view of the oral hygiene device of FIG. 3A.
Figure 3C:
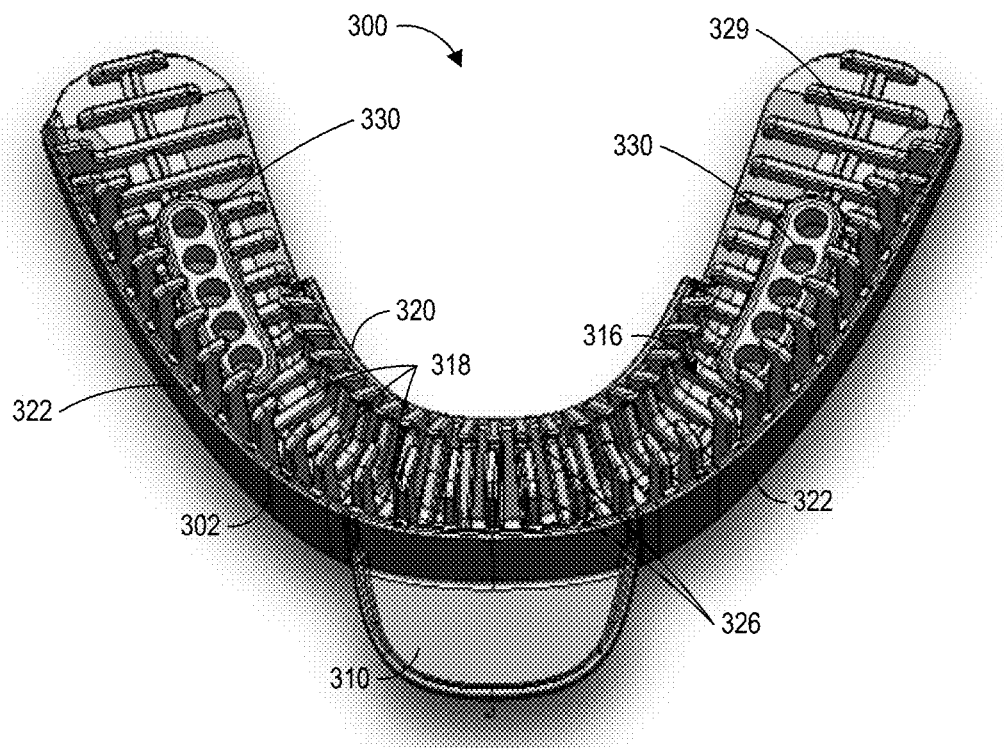
FIG. 3C is a top and front perspective view of the oral hygiene device of FIG. 3A.
Figure 3D:
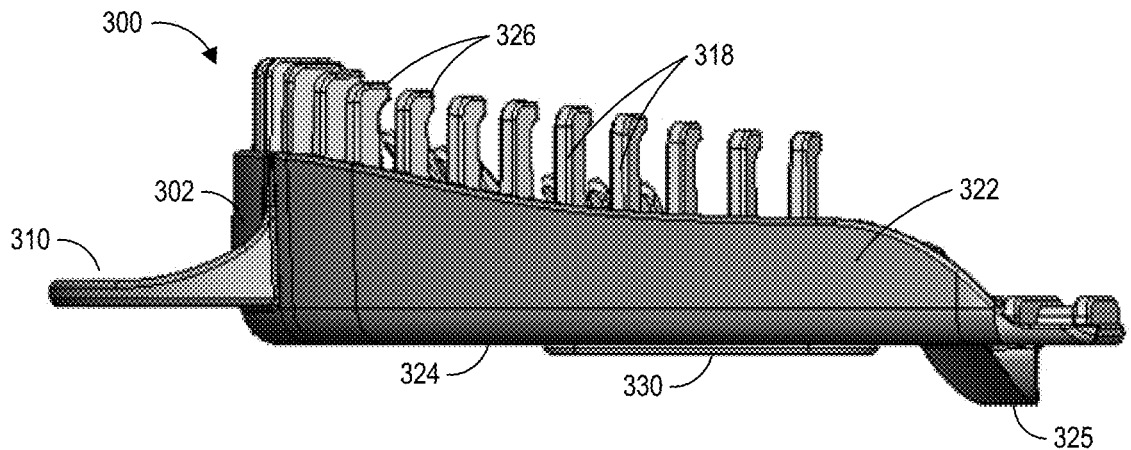
FIG. 3D is a side view of the oral hygiene device of FIG. 3A.
Figure 3E:
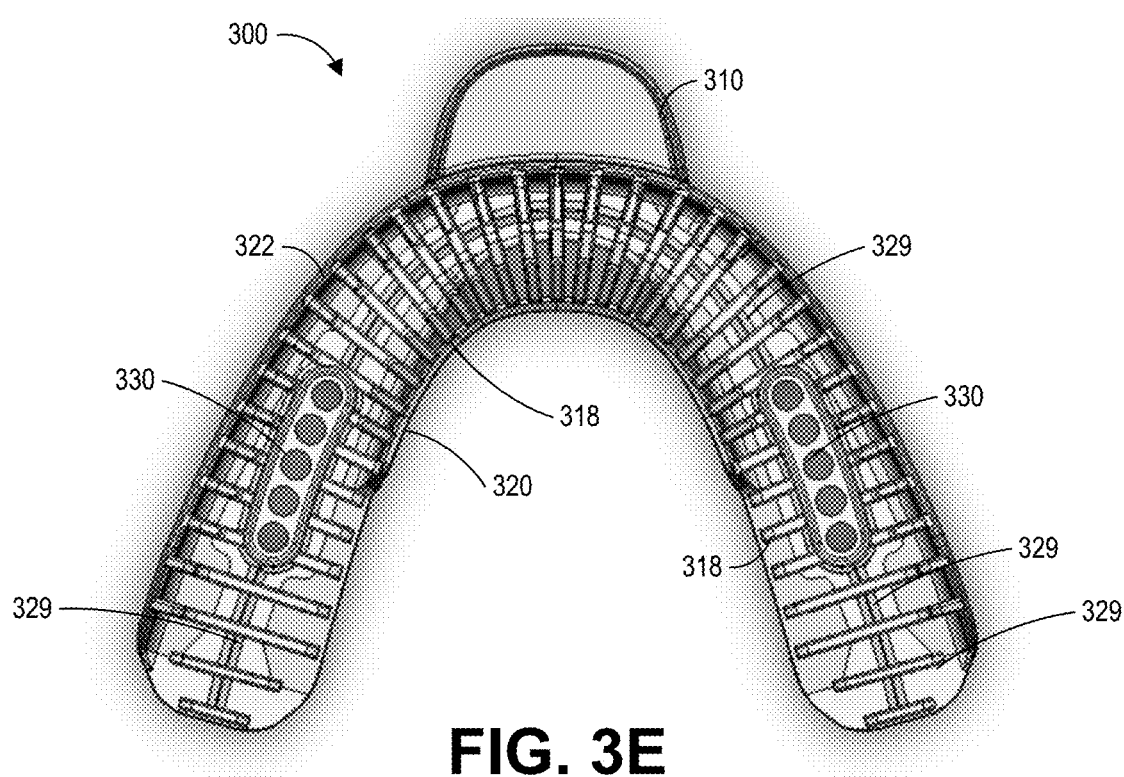
FIG. 3E is a top view of the oral hygiene device of FIG. 3A.
Figure 3F:
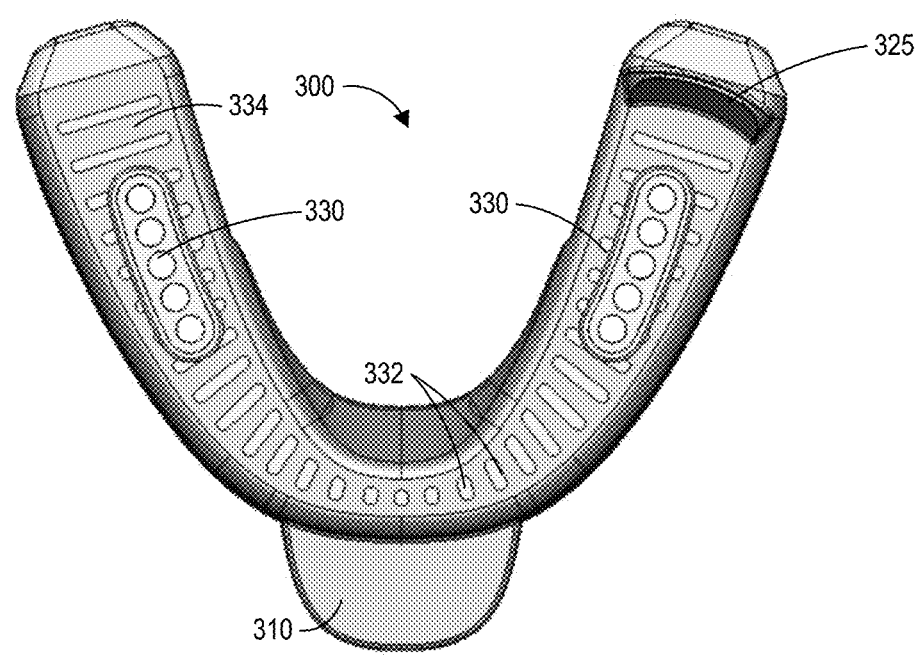
FIG. 3F is a bottom view of the oral hygiene device of FIG. 3A.
Figure 3G:
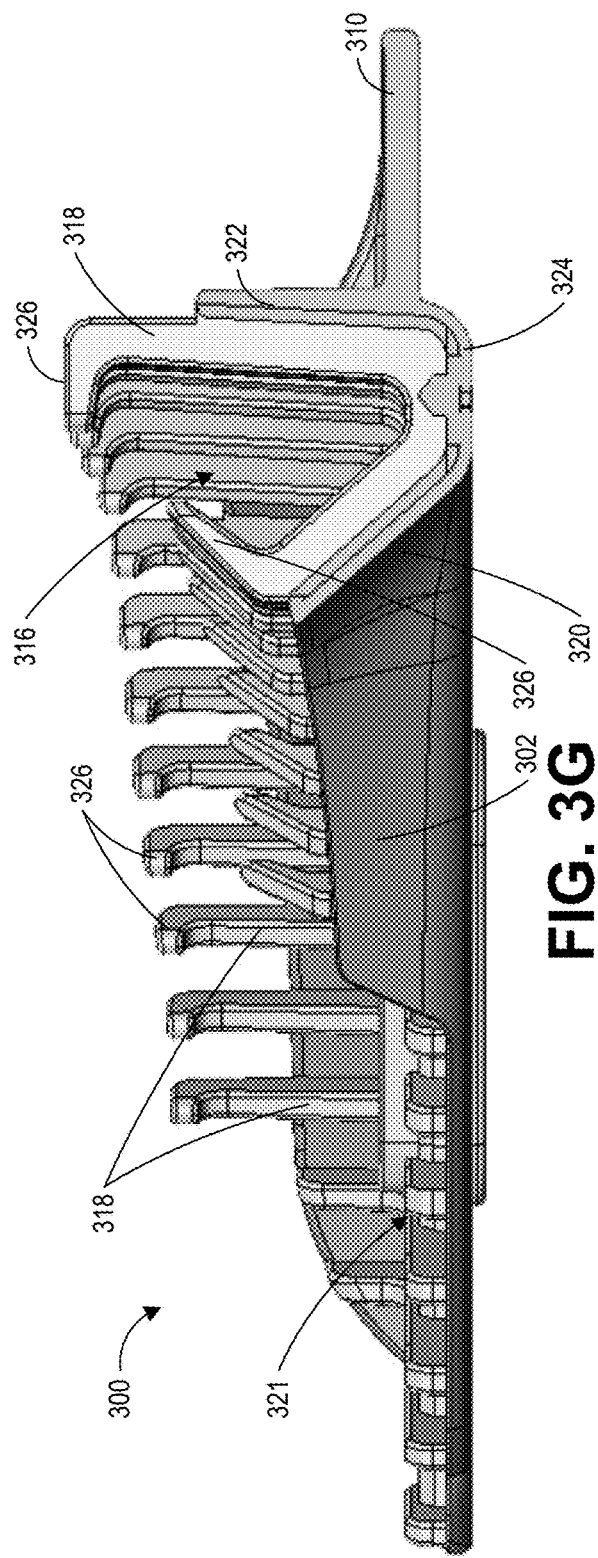
FIG. 3G is a first cross-sectional view of the oral hygiene device of FIG. 3A.
Figure 3H:
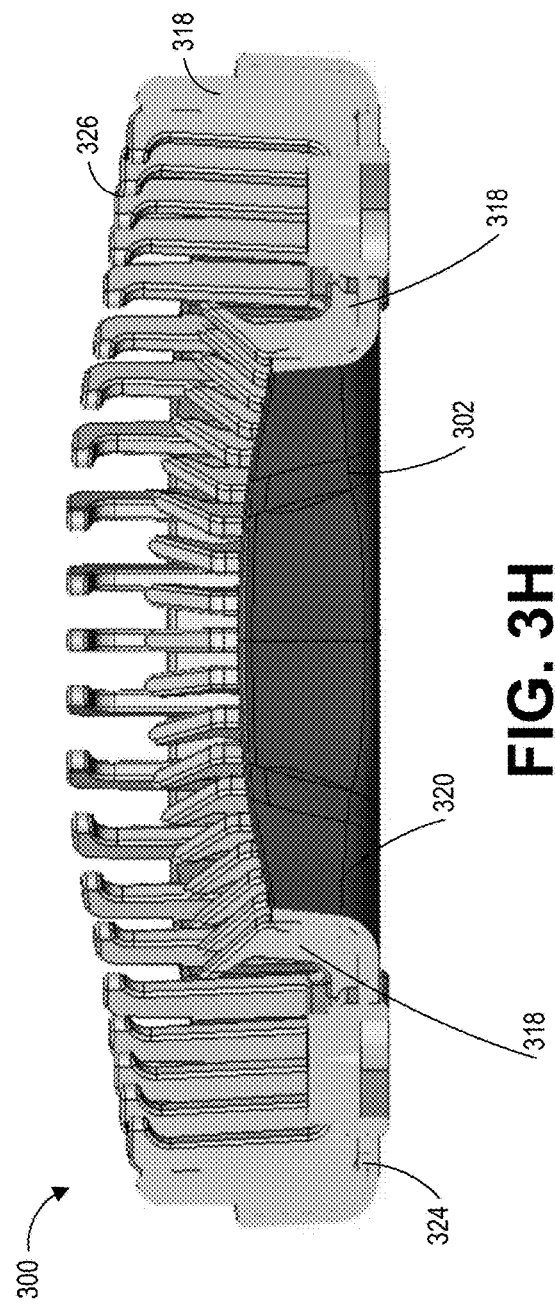
FIG. 3H is a second cross-sectional view of the oral hygiene device of FIG. 3A.
Figure 3I:
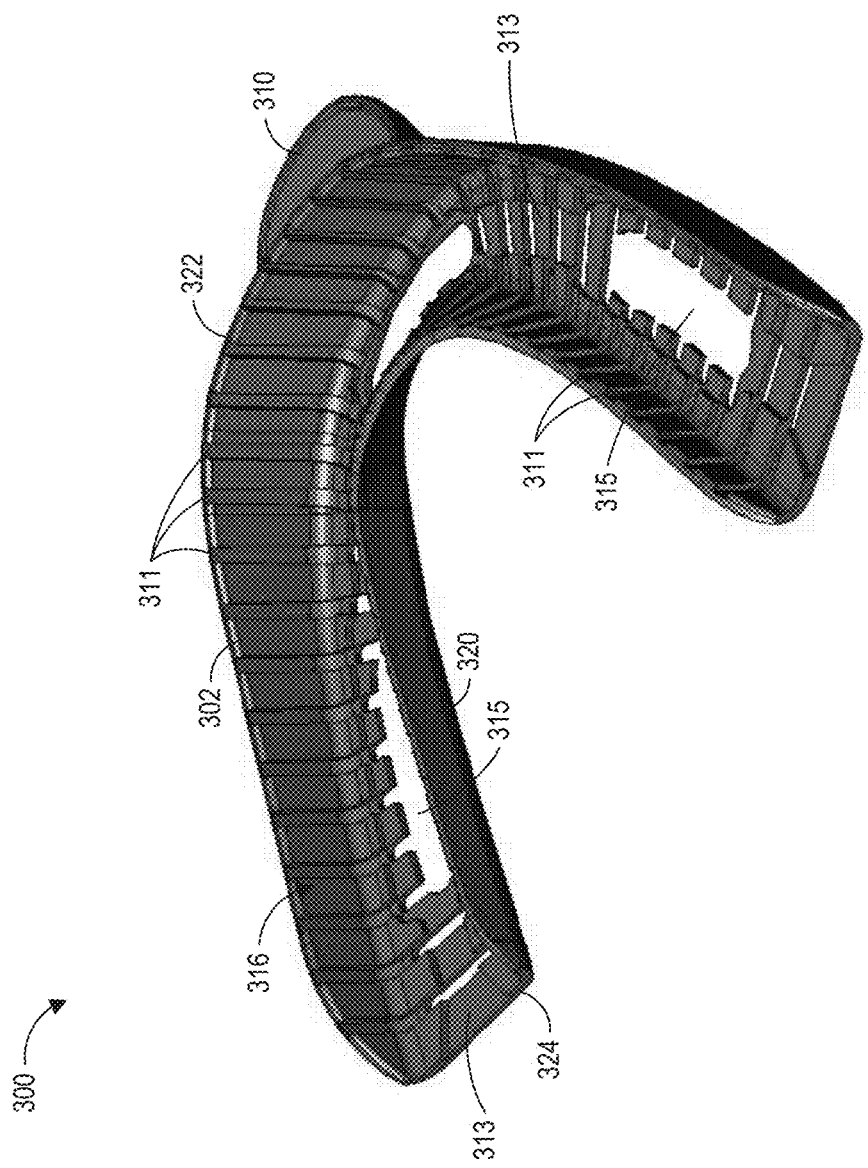
FIG. 3I illustrates a perspective view of the body of the oral hygiene device of FIG. 3A.
Figure 3J:
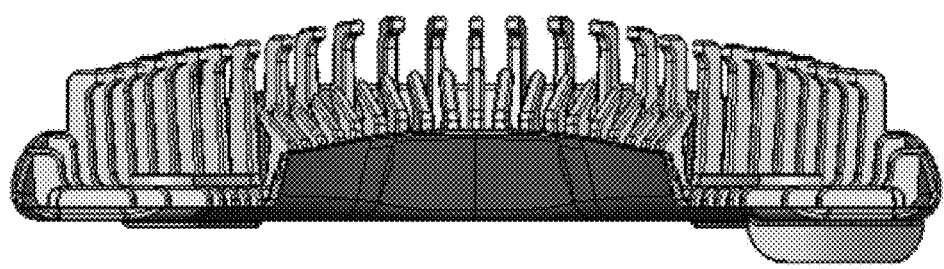
FIG. 3J is a back view of the oral hygiene device of FIG. 3A.
Figure 3K:
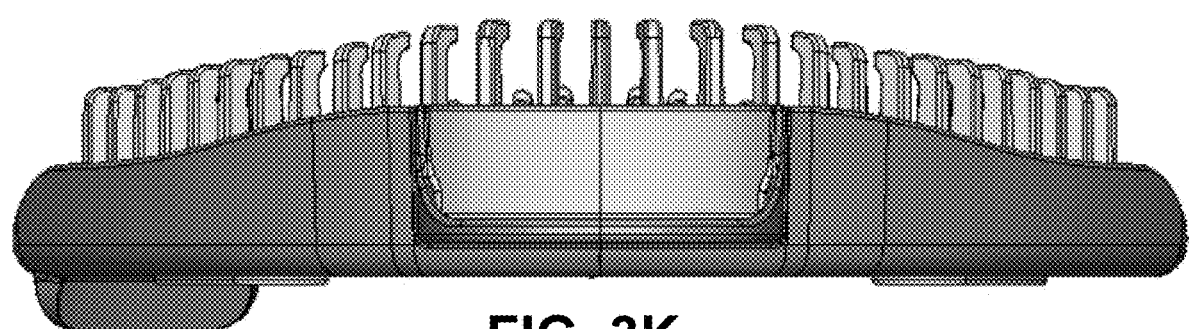
FIG. 3K is a front view of the oral hygiene device of FIG. 3A.

FIGS. 3A-3K illustrate views of another embodiment of an oral hygiene device 300. In some respects, the oral hygiene device 300 is similar to the oral hygiene device 100b shown in FIG. 2B, because the oral hygiene device 300 of FIGS. 3A-3I may similarly be configured for cleaning only the user's upper teeth and associated orthodontia or the user's lower teeth and associated orthodontia at a time. The oral hygiene device 300 can be used, for example, to clean the user's upper teeth and then can be flipped over and used to clean the user's lower teeth, or vice versa. FIG. 3A is a top and side perspective view, FIG. 3B is a bottom and side perspective view, FIG. 3C is a top and front perspective view, FIG. 3D is a side view, FIG. 3E is a top view, FIG. 3F is a bottom view, FIG. 3G is a first cross-sectional view, and FIG. 3G is a second cross-sectional view of the oral hygiene device 300. FIG. 3I illustrates a perspective view of the body 302 of the oral hygiene device 300. FIGS. 3J and 3K are back and front view so of the device 300.

With reference to FIGS. 3A-3I, the oral hygiene device 300 includes a body 302. The body 302 is shown alone in FIG. 3I and in FIGS. 3A-3H with additional teeth and orthodontia cleaning features molded thereon. In the illustrated embodiment, the body 302 is generally U-shaped similar to the oral hygiene devices described previously. For example, the generally U-shaped body 302 can be configured to generally follow the shape of a user's upper and/or lower teeth. As illustrated, the body 302 also includes a generally U-shaped cross-sectional profile, similar to the oral hygiene devices 100b, 200 (and others) described above. The generally U-shaped cross-sectional profile may include an inner wall 320, an outer wall 322, and a bottom wall 324 as shown. The generally U-shaped cross-sectional profile can define a channel 316 within the body 302. The channel 316 can be formed between the inner wall 320 and the outer wall 322 and bounded below by the bottom wall 324. In some embodiments, the body 302 can be configured in size and shape such that the channel 316 is configured to receive the user's upper teeth or lower teeth during use of the oral hygiene device 300.

As shown in the cross-sectional views of FIGS. 3G and 3H, the shape of the channel 316 may vary at different positions of the body 302. For example, as shown in FIG. 3G, at the front of the body 302, the inner wall 320 may be formed at an angle with respect to the bottom wall 324. In some embodiments, the angle is between 30 and 60 degrees, between 40 and 50 degrees, or about 45 degrees. As shown, the outer wall 322 can extend at a substantially 90-degree angle (for example, 90 degrees plus or minus 5 or 10 degrees) with respect to the bottom wall 324. This shape allows the body 302 to fit comfortably over the user's front teeth, which generally comprises substantially vertical front surfaces and sloping, angled rear surfaces.

FIG. 3H is a cross-sectional view of the oral hygiene device 300 taken through a rear portion of the device. As shown, at this position, both of the inner and outer walls 320, 324 are positioned at a substantially 90-degree angle (for example, 90 degrees plus or minus 5 or 10 degrees) with respect to the bottom wall 324. This shape can facilitate a good fit over the user's back teeth (e.g., molars), which are generally more rectangular in shape. Comparing FIGS. 3G and 3H, one can also see that, in the illustrated embodiment, the width of channel 316 can narrow from the rear of channel (FIG. 3H) toward the front of the channel (FIG. 3G). Again, this shape can facilitate fit with the user's teeth.

An additional feature that can facilitate good fit for the device 300 is visible in FIGS. 3G and 3H. As shown, the inner wall 320 can be shorter than the outer wall 322. This shape may be beneficial due to the anatomy of the mouth due to the upper palate, lower jaw, and tongue. In some instances, users may experience pain or discomfort if the inner wall 320 and the outer wall 322 are the same height or if the inner wall 320 is too tall. Accordingly, in some embodiments, the inner wall 320 is less than 10 mm, less than 8 mm, less than 6 mm, less than 5 mm, or less than 4 mm tall. In some embodiments, the heights of inner wall 320 and the outer wall 322 can increase from the back towards the front of the body 302.

As best shown in FIGS. 3A-3C and 3G, the device 300 can include a cutout 321 on a rear portion of the lingual or inner wall 320. That is, as shown, the inner wall 320 may not extend entirely towards the back of the device 300. It has been found during testing, that inclusion of the cutout 321 facilitates use of the device, allowing it to clear the user's teeth better. For example, the cutout 321 can allow the device 300 to have an increased range of motion as it is moved side to side in the mouth. This can also increase the comfort of the device as the inner wall 321 has been reduced in the rear portion of the device so as to not interfere or undesirably contact the mouth during use. Additionally, in some embodiments, inclusion of the cutout 321 can allow the device 300 to fit a wider range of mouth sizes and shapes.

The body 302 may be made of a rigid, semi-rigid, or flexible material, such as plastic, rubber, a polymer, or other suitable material. In some embodiments, the body 302 is rigid enough to provide general support and shape for the oral hygiene device 300, while remaining flexible enough to allow the body 302 to fit to the particular anatomy of the user's mouth and teeth. In some embodiments, the body 302 comprises a thermoplastic elastomer (TPE), high-density polyethylene (HDPE), polypropylene (PP), low-density polyethylene (LDPE), polyamides, polyolefin or other resins, polychloro-trifluoroethylene, various thermoplastics, and/or various elastomers. In some embodiments, the body 302 may comprise a food grade polypropylene. The composition of the body 302 is not limited to the above materials, but is selected for specific characteristics including enough rigidity to provide general support and shape for the oral hygiene device 300, while including enough flexibility to allow the body 202 to fit to the particular anatomy of the user's mouth and teeth.

The body 302 may be formed such that the walls (e.g., the inner wall 320, the outer wall 322, and the bottom wall 324) are sufficiently thin so as to allow the body 302 to flex and conform to the shape of the user's mouth. For example, in some embodiments, the walls of the body 202 are about 2 mm, 1.5 mm, 1.0 mm, 0.75 mm, 0.5, or 0.25 mm thick. In some embodiments, the nominal thickness of the walls of the body 302 is about 1.2 mm. These thicknesses are provided by way of example, and the thickness of the walls of the body 302 can be selected to provide the desired characteristics described throughout this application.

FIG. 3I illustrates the body 302 alone. As shown in FIG. 3I, the body 302 can include a number of features formed within the channel 316 on the inner surfaces of the inner wall 320, the outer wall 320, and the bottom wall 324. As illustrated, the body 302 includes a plurality of grooves 311 formed within the channel. As illustrated, the grooves 311 can extend up and down the inner and outer walls 320 and along the bottom wall 324. The grooves 311 can be configured to receive the teeth cleaning features of the oral hygiene device 300, such as the ribs 318 described below. As such, the spacing of the grooves can be configured to match the spacing of the ribs 318 as will be described below. In some embodiments, for example, as illustrated, the body 302 may also comprise an indention 313 that extends along the inner surface of the bottom wall 324 as shown. The indention 313 can be configured to receive the spline 329, which is described below. FIG. 3I also illustrates that one or more apertures 715 can be formed through the bottom wall 324. As will be described below the apertures 715 can be configured to receive wells for holding beads or dabs of cleaning and/or freshening material.

In some embodiments, the oral hygiene device 300 can be provided in a variety of sizes (e.g., small, medium, large, adult, or child) configured for use by users that have different size mouths. In some embodiments, the oral hygiene device 300 can be provided in a size that is generally configured to fit most mouth sizes. For example, in some embodiments, the device 300 may comprise a width configured to fit mouths with a molar to molar width of about 50 mm to 65 mm, about 50 mm to 62 mm, about 52 mm to 58 mm, or about 54 mm to 56 mm. The device 300 may comprise a length configured to fit mouths with a front tooth to rear molar length of between 40 mm and 55 mm, between 40 and 50 mm, or between 43 and 49 mm. In some embodiments, the width of the device 300 is at least 62 mm. Measurements of many mouths were taken between the buccal of the second molar on the right and the buccal of the second molar of the left of the upper teeth. 62 mm was determined to be widest measurement.

As illustrated, the oral hygiene device 300 includes a handle 310. The handle 310 can be configured as a tab, although other shapes are possible. The handle 310 can extend from a front portion of the body 302 so as to be able to extend out of the user's mouth between the user's lips when the oral hygiene device 300 is inserted into the user's mouth. In the illustrated embodiment, the handle 310 extends form the outer wall 322 of the body 302 at a position between the bottom wall 324 and the top of the outer wall 322. Alternatively, the handle 310 may be aligned with the bottom wall 324 of the body 302, or the handle 310 can be placed in any other desired location. In some embodiments, the oral hygiene device 300 does not include a handle 310 (i.e., the handle 310 may be omitted). Similar to the discussion above, the user may use the handle to manipulate the oral hygiene device 300 to use the oral hygiene device 300 to clean the user's teeth. In some embodiments, the handle 310 comprises a length of 11 mm and a width of 22 mm. However, other shapes of the handle 310 are also possible. For example, a longer handle 310 could be used that extends further out of the mouth. This may provide an easier hold for people with dexterity problems. This may also provide easier access to a caregiver using the device 300 on another person. For example, the caregiver may not have to put their fingers into the person's mouth.

Similar to the oral hygiene devices 100a, 100b, and others described generally above, the oral hygiene device 300 can include teeth and orthodontia cleaning features configured to clean the user's teeth when the device is used. In the illustrated embodiment, the teeth cleaning features comprise the ribs 318, although in other embodiments, other types of teeth cleaning features (e.g., foam, bristles, textured surfaces, etc.) can be used in addition to or in place of the ribs 318.

The ribs 318 can be formed of the same material as the body 302, or the ribs 318 can be formed of a softer or more flexible material than the body 302 as described above. Advantageously, forming the body 302 and the ribs 318 of different materials may improve functionality, comfort, and efficiency of the device. For example, as described above the body 302 can be formed of a generally stiffer and more rigid material to provide structural support for the device 300, while the ribs 318 can be formed of a generally less rigid or softer material. The softer material of the ribs 318 can provide more user comfort during use, while also better conforming to the user's mouth and teeth shape to provide increased cleaning efficiency.

The ribs 318 can be integrally formed with the body 302 or can be separately formed and attached to the body 302. In some embodiments, the body 302 and ribs 318 are co-molded in a two-step molding process, such as a double shot or overmolding process, as described above. In other embodiments, the body 302 and the ribs 318 can be formed separately and then attached to one another. In some embodiments, the ribs 318 comprise a thermoplastic elastomer (TPE), silicon rubber, high-density polyethylene (HDPE), polypropylene (PP), low-density polyethylene (LDPE), polyamides, polychlorotrifluoroethylene, various thermoplastics, and/or various elastomers. In some embodiments, the ribs 318 comprise a food grade TPE or thermoplastic polyurethane (TPU). The composition of the ribs 318 is not limited to the above materials, but can be selected for specific characteristics including the ability to clean on and around teeth. In some embodiments, the ribs 318 may comprise a material with a Shore A hardness of between 70 and 100, between 75 and 95, or between 80 and 90, or between 85 and 90. Shore A hardnesses within these ranges can provide the comfort and efficiency advantages discussed above.

In the illustrated embodiment, the ribs 318 are positioned within the channel 316. In some embodiments, the shape of the ribs 318 can be formed in order to contour to a user's mouth and teeth. In some embodiments, the ribs 318 are about 1.2 mm, 1.0 mm, 0.8 mm, 0.6 mm, or 0.5 mm thick, although other thicknesses, both thinner and thicker than these example values are possible. The thickness can be selected to facilitate teeth cleaning efficiency and/or user comfort.

In some embodiments, the size and shape of the ribs 318 varies depending upon the location of the ribs 318 on the body 302. For example, the size and shape of the ribs 318 can be adjusted to suit the general size and shape of the particular teeth the ribs 318 will generally overlie when the oral hygiene device 300 is positioned within the mouth. Ribs 318 that are positioned on the body 302 to generally overlie molars (which are generally wider) may have a different shape than ribs 318 that are positioned to overlie incisors (which are generally thinner). The ribs 318 can also be configured such that they contact more than one surface of the user's teeth at a time. For example, the ribs 318 can be configured to contact the front, bottom and back surfaces of the user's upper teeth and/or the front, top, and back surfaces of the user's teeth simultaneously.

These features can be seen, for example, in the cross-sectional views of FIGS. 3H and 7G. As noted above, FIGS. 3G and 3H illustrate that the cross-sectional shape of the body 302 can vary from the back to the front of the device 300. As the ribs 318 are formed on the body 302, the shape of the ribs 318 can also vary from the back to the front. For example, as shown in FIG. 3G, the inner portion of the ribs 318 at the front of the device can be formed at an angle with respect to the bottom wall 324. In some embodiments, the angle is between 30 and 60 degrees, between 40 and 50 degrees, or about 45 degrees. As shown, an outer portion of the ribs 318 at the front of the device can extend at a substantially 90-degree angle (for example, 90 degrees plus or minus 5 or 10 degrees) with respect to the bottom wall 324. This shape can follow the shape of the channel 316 as described above and facilitate fit and user comfort. As shown in FIG. 3H, both the inner and outer portions of the ribs 318 at the rear of the device 300 can extend at a substantially 90-degree angle (for example, 90 degrees plus or minus 5 or 10 degrees) with respect to the bottom wall 324. Again, this shape follows the shape of the channel 316 and can provide good fit and comfort.

The ribs 318 may also have a shape that is adapted to clean the user's teeth, gums, and/or gum line around orthodontia that is adhered to the teeth, such as brackets. In the illustrated embodiment, the oral hygiene device 300 includes ribs 318 positioned within the channel 316. The ribs 318 positioned within the channel 316 can be configured to clean the upper and/or lower teeth of the user depending upon the orientation of the device 300. As illustrated, ribs 318 extend generally across the channel 316 from the inner wall 320 to the outer wall 322, as well as along the inner surfaces of the inner wall 320 and the outer wall 322. Such a configuration can allow the ribs to contact multiple surfaces of the user's teeth simultaneously as described above. In some embodiments, the shape of the individual ribs 318 may be varied to suit the particular teeth and orthodontia the ribs will contact during use. For example, as illustrated, the ribs 318 positioned within the back parts of the channel 316 (i.e., the ribs configured to clean molars) can have a wider cutout shape configured to match the thickness of the molars, and the ribs 318 positioned within the front part of the channel 316 (i.e., the ribs configured to contact incisors) have a narrower cutout shape configured to match the thickness of the incisors).

The one or more of the ribs 318 can include fingers 326 extending therefrom. The fingers 326 may be angled with respect to the gums so as to clean the space between the gums and the teeth. The fingers 326 be configured as protrusions or extensions that extend from the ribs 318. In some embodiments, the fingers 326 can be configured to above, below, and/or in between orthodontia. In some embodiments, the fingers 326 can be angled inwardly at an angle of about 90 degrees (e.g., plus or minus 5, 10, 15, or 20 degrees so as to be able to clean above and/or below brackets adhered to the user's teeth.

Such ribs can specifically target mechanical removal of plaque from the bracket apical to the gum line The device 300 can be used in a side-to-side motion. It places the ribs in contact and ensures plaque removal in this hard to access location. Mechanical removal is the best solution to remove this plaque. Electric toothbrushes, floss threaders, interdental cleaners do not have the singular focus in this area but are better suited for overall oral care. Other treatments such as 0.5% sodium fluoride, fluoride varnish, and chlorhexidine would be much more effective if the plaque/biofilm were removed, and the natural enamel was exposed so to allow better contact.

In some embodiments, the ribs 318 can be smaller or omitted at the rear ends of the oral hygiene device 300. For example, as shown in FIG. 3A, the last four ribs 318 on each end of the device 300 do not include the fingers 326. Thus, in the illustrated embodiment, the last four ribs 318 on each ends are smaller than the remaining ribs 318 on the device. In some embodiments, the ribs on the last 10 mm, 9 mm, 8 mm, 7 mm, 6 mm, or 5 mm of the device 300 can be smaller or omitted as shown. This can facilitate fit of the device 300 in the user's mouth and improve user comfort.

Moreover, in some embodiments, the rear most portions of the device 300 can be made from the same material as the ribs 318. Thus, the rearmost portions can be softer than body 302. For example, comparing FIGS. 3A and 3B to FIG. 3I, one can see that the rear most portions of the device 300 can extend beyond the rear most portions of the body 302. This can facilitate user comfort and accommodate different size mouths.

In the illustrated embodiment, the oral hygiene device 300 includes about 35 ribs in the channel 316, although other numbers are possible (e.g., about 15, about 20, about 25, about 30, about 35, about 40, about 45, or about 50 ribs 318). The ribs 318 may be spaced evenly or unevenly. In some embodiments, the ribs 318 are spaced apart so as to be aligned with the spaces between the user's teeth or the interproximal contact area (IPC) when the oral hygiene device 300 is inserted into the mouth. In some embodiments, there can be more ribs 318 disposed in the channel 316 than there are upper teeth. This can provide additional coverage for teeth cleaning and can reduce the amount a user would need to move the oral hygiene device 300 in order to contact and adequately clean all the teeth. In some embodiments, the ribs 318 are spaced about 2 mm, 4 mm, 6 mm, 8 mm, or 10 mm apart, although other spacings are possible. The position and spacing of the ribs 318 can be selected to facilitate operation of the device. For example, the ribs 318 can be positioned so as to efficiently clean the teeth. In some embodiments, the spacing of the ribs 318 is a function of the average dimensions of each tooth.

The ribs 318 positioned within the channel 316 may be connected by a spline 329 as shown, for example, in FIG. 3E. The spline 329 can be configured to clean the occlusal surface of the teeth. The spline 329 can be positioned within the channel 316 on the bottom wall 324. In some embodiments, the spline 329 runs continuously from one end of the channel 316 to the other. The shape, size, materials, and placement of the spline 329 can be based on specific desirable characteristics, such as the ability to clean the occlusal surface of each tooth. The spline 329 may interconnect the ribs 318. The spline 329 can be formed from the same material as the ribs 318.

The oral hygiene device 300 may also include reservoirs 330 for holding beads or dabs of a cleaning or freshening material as described below. In the illustrated embodiment, the device 300 includes two reservoirs 330 that extend through the apertures 315 of the body 302. As shown, the two reservoirs 330 can be positioned toward the rear of the device 300. These positions for the reservoirs 330 may work well to release the material of the dabs or beads over the much or all of the user's mouth or teeth and provide good coverage. Other numbers of reservoirs 330 and other positions for the reservoirs 330 are also possible. The reservoirs 330 can be formed from the same material as the spline 329 and the ribs 318. As shown in the figures, in some embodiments, the reservoirs 330 extend above and below the bottom wall 324. This may facilitate release of the bead or dab material. For example, in some embodiments, the reservoirs 330 may extend at least 0.5 mm, at least 1.0 mm, or at least 1.5 mm above and/or below the body 302.

As illustrated, in some embodiments, the reservoirs 330 can include within them one or more openings that extend therethrough. The openings may facilitate release of the bead or dab material both above and below the device 300 during use. In the illustrated embodiment, the two reservoirs 330 can include five openings. The size and number of the openings through the reservoirs 330 can be configured to release of the bead or dab material.

As shown in FIGS. 3B and 3F, the device 300 can include tongue cleaning features formed on the bottom surface of the bottom wall 324. As illustrated, the tongue cleaning features can comprise ridges 332 that project slightly downward from the bottom wall 324. The ridges 332 can extend downwardly from the bottom wall 324 of the body 302. In some embodiments, the ridges 332 extend at least 0.25 mm, at least 0.5 mm, at least 0.75 mm, at least 1.0 mm, at least 1.25 mm, at least 1.5 mm, or at least 2.0 mm below the bottom wall 324 of the body 302. The ridges 332 can be configured to scrape and/or clean the user's tongue as will be described in more detail below. The ridges 332 can be formed of the same material as the ribs 318. Although the tongue cleaning features are illustrated as ridges 332 in FIGS. 3A-3H, other tongue cleaning features can also be used in other embodiments.

The device 300 may also include embodiment of a tongue cleaner 325 that can be integrated into the device. As shown, the tongue cleaner 325 can be positioned on a bottom surface of the body of the device. The tongue cleaner 325 may be formed of a rigid material (such as the same material as the body) and may comprise a shape that can be used to scrape or clean the tongue.

The oral hygiene device 300 can be configured to be used to clean and/or freshen a user's mouth, teeth, and tongue and clean around orthodontia. An example method of use for the device 300 will now be described. In this example, the device 300 can be inserted into the user's mouth. The user may hold the device 300 using the handle 310. The device 300 can be inserted into the mouth such that the user's upper teeth and upper orthodontia or the user's lower teeth and lower orthodontia are positioned within the channel 316. For example, the user's upper teeth and orthodontia can be positioned within the channel 316. With the device 300 so positioned, the user may manipulate the device 300 to freshen the mouth. For example, the user may manipulate the device 300 by moving the device 300 side-to-side and back-and-forth. During this motion, the ribs 318 can contact and clean the surfaces of the user's teeth around. At the same time the fingers 326 can contact and clean the user's gum line and/or around the orthodontia. The motion can produce similar effects as the Bass technique described above. Further, while using the device, the dab and bead material device can be naturally released, providing additional cleaning and/or freshening for the mouth.

In some embodiments, while cleaning the user's upper teeth, the teeth cleaning features (ridges 332) of the bottom wall 324 of the device 300 can clean the user's tongue. This can be accomplished by moving the ridges 332 across the surface of the user's tongue. Advantageously, the bead or dab material can be released from the reservoir 330 onto the user's tongue providing additional freshening.

After the user's upper teeth and tongue are cleaned, the user can flip the device 300, such that the user's lower teeth are received within the groove 316. The device can then be used in a similar manner to clean the user's lower teeth. In some embodiments, the user's lower teeth can be cleaned first, before cleaning the user's upper teeth.

In some embodiments, the cutout 321 extends at least, at most, or about 10%, 20%, 25%, 30%, 33%, 40%, 50%, or 60% of the length of the back wall, measured from the rear most portion of the device 300 towards the front most portion of the device.

In some embodiments, the device 300 may comprise one or more materials having a durometer of 60 Shore A, 75 Shore A, and 90 Shore A. These durometers can refer to the material that comprises the body and/or the ribs of the device 300 Other durometers may also be used as described above.

Additionally, in some embodiments, the surface finish of the device 300 (e.g., the surface finish of the ribs or other portions of the device that contact the teeth during use) can be configured to have a degree of roughness. The roughness may further facilitate cleaning, such as removal of plaque. In some embodiments, the surface finish comprises an EDM (electrical discharge machining) surface finish. The surface finish may comprise, for example, a VDI surface finish of 30 (123 microinches). Other surface finishes can also be used.

Within the reservoirs 330, the oral hygiene device 300 can include beads of mouthwash, breath freshener, toothpaste, desensitizing paste or gel, or whitening paste or gel. In some embodiments, the beads are referred to as "dabs." As mentioned previously, in some embodiments, the oral hygiene devices described herein are configured to be useable without water or toothpaste, as such the beads of mouthwash, breath freshener, toothpaste, desensitizing paste or gel, or whitening paste or gel can be configured to also be useable without requiring water and/or without requiring the user to rinse out his or her mouth after use. Alternatively, in some embodiments, the beads can comprise beads of a dentifrice that can be used with water during use of the device. The size, shape, materials, and location of the beads is selected for specific characteristics including the ability to freshen breath or clean the mouth.

In some embodiments, the beads of mouthwash, breath freshener, toothpaste, desensitizing paste or gel, or whitening paste or gel are positioned on the oral hygiene device so as to be automatically activated when the oral hygiene device is used by the user. In some embodiments, the beads are activated by biting, grinding, or crushing by the user's teeth during use of the oral hygiene device. In some embodiments, the beads 640 dissolve into the mouth during use.

In some embodiments, the beads or dabs can comprise a formulation configured to clean and freshen one's mouth, and that can be used without water. In some embodiments, the beads or dabs comprise a formulation that is safe to be swallowed. This can allow a user to quickly and easily use the oral hygiene devices anywhere. In other embodiments, the beads or dabs can comprise formulations that are not safe to be swallowed (such as formulations that include fluoride or mouthwash). Several example formulations are shown in the following tables.

| Sample Formulation 1 | | | |
|---|---|---|---|
| Ingredient | % w/w | g/batch | Function |
| Xanthan Gum | 0.500 | 0.500 | Viscosity Builder |
| Poloxamer P407 | 30.000 | 30.000 | Gelling Agent |
| Glycerin | 10.000 | 10.000 | Humectant |
| Xylitol | 10.000 | 10.000 | sweetener |
| SLS | 1.500 | 1.500 | Foaming |
| FD&C Blue 2 | 0.050 | 0.050 | Color |
| Mint | 2.000 | 2.000 | Flavor |
| Water | 45.950 | 45.950 | Solvent |

| Sample Formulation 2 | | | |
|---|---|---|---|
| Ingredient | % w/w | g/batch | Function |
| Xanthan Gum | 0.500 | 0.500 | Viscosity Builder |
| Poloxamer P407 | 25.000 | 25.000 | Gelling Agent |
| Glycerin | 10.000 | 10.000 | Humectant |
| Xylitol | 10.000 | 10.000 | sweetener |
| SLS | 1.500 | 1.500 | Foaming |
| FD&C Blue 2 | 0.050 | 0.050 | Color |
| Mint | 1.000 | 1.000 | Flavor |
| Water | 51.950 | 51.950 | Solvent |

| Sample Formulation 3 | | | |
|---|---|---|---|
| Ingredient | % w/w | g/batch | Function |
| Xanthan Gum | 0.500 | 0.500 | Viscosity Builder |
| Poloxamer P407 | 25.000 | 25.000 | Gelling Agent |
| Glycerin | 10.000 | 10.000 | Humectant |
| Sucralose | 0.125 | 0.125 | sweetener |
| SLS | 1.500 | 1.500 | Foaming |
| FD&C Blue 2 | 0.050 | 0.050 | Color |
| Mint | 1.500 | 1.500 | Flavor |
| Water | 61.325 | 61.325 | Solvent |

Sample Formulation 4

| Ingredient | % w/w | g/batch | Function |
|---|---|---|---|
| Xanthan Gum | 0.750 | 0.750 | Viscosity Builder |
| Poloxamer P407 | 20.000 | 20.000 | Gelling Agent |
| Glycerin | 10.000 | 10.000 | Humectant |
| Sucralose | 0.125 | 0.125 | sweetener |
| SLS | 1.000 | 1.000 | Foaming |
| FD&C Blue 2 | 0.050 | 0.050 | Color |
| Mint | 1.500 | 1.500 | Flavor |
| Water | 66.575 | 66.575 | Solvent |

Sample Formulation 5

| Ingredient | % w/w | g/batch | Function |
|---|---|---|---|
| Xanthan Gum | 1.000 | 1.000 | Viscosity Builder |
| Poloxamer P407 | 15.000 | 15.000 | Gelling Agent |
| Glycerin | 10.000 | 10.000 | Humectant |
| Sucralose | 0.125 | 0.125 | sweetener |
| SLS | 1.000 | 1.000 | Foaming |
| FD&C Blue 2 | 0.050 | 0.050 | Color |
| Mint | 1.500 | 1.500 | Flavor |
| Water | 71.325 | 71.325 | Solvent |

Sample Formulation 6

| Ingredient | % w/w | g/batch | Function |
|---|---|---|---|
| Xanthan Gum | 1.000 | 1.000 | Viscosity Builder |
| Poloxamer P407 | 18.000 | 18.000 | Gelling Agent |
| Glycerin | 10.000 | 10.000 | Humectant |
| Sucralose | 0.125 | 0.125 | sweetener |
| SLS | 0.500 | 0.500 | Foaming |
| FD&C Blue 2 | 0.050 | 0.050 | Color |
| Mint | 1.500 | 1.500 | Flavor |
| Water | 68.825 | 68.825 | Solvent |

Sample Formulation 7

| Ingredient | % w/w | g/batch | Function |
|---|---|---|---|
| Xanthan Gum | 1.000 | 1.000 | Viscosity Builder |
| Poloxamer P407 | 18.000 | 18.000 | Gelling Agent |
| Glycerin | 10.000 | 10.000 | Humectant |
| Sucralose | 0.125 | 0.125 | sweetener |
| SLS | 0.500 | 0.500 | Foaming |
| Green DB-110004 | 0.005 | 0.005 | Color - Dye Blend |
| Mint | 1.500 | 1.500 | Flavor |
| Water | 68.870 | 68.870 | Solvent |

Sample Formulation 8

| Ingredient | % w/w | g/batch | Function |
|---|---|---|---|
| Xanthan Gum | 1.000 | 1.000 | Viscosity Builder |
| Poloxamer P407 | 18.000 | 18.000 | Gelling Agent |
| Glycerin | 10.000 | 10.000 | Humectant |
| Sucralose | 0.125 | 0.125 | Sweetener |
| SLS | 0.500 | 0.500 | Foaming |
| Green DB-110004 | 0.005 | 0.005 | Color - Dye Blend |
| Menthol | 0.500 | 0.500 | Flavor |
| Water | 69.870 | 69.870 | Solvent |

Sample Formulation 9

| Function | Ingredient | % w/w | g/batch |
|---|---|---|---|
| Viscosity Builder | Xanthan Gum | 1.000 | 1.000 |
| Gelling Agent | Poloxamer P407 | 18.000 | 18.000 |
| Humectant | Glycerin | 10.000 | 10.000 |
| sweetener | Sucralose | 0.125 | 0.125 |
| Foaming | SLS | 0.500 | 0.500 |
| Color - Dye Blend | Green DB-110004 | 0.005 | 0.005 |
| Flavor | Menthol | 0.750 | 0.750 |
| Solvent | Water | 69.620 | 69.620 |

While any of the above-listed sample formulations are useable in the beads or dabs, testing has revealed that sample formulation 8 and sample formulation 9, which include menthol as a flavorant at 0.50% w/w and 0.75% w/w, respectively, are potent, and can provide a strong burst of freshener, which can be desirable.

Although the beads are depicted in the oral hygiene device 600, a person of skill in the art, guided by this disclosure, would understand that the beads 640 can be incorporated into any of the various embodiments of the oral hygiene device described herein. The beads may also comprise fluoride, iodine, or chlorohexidine, among other things. In some embodiments, the mouth wash or breath freshener can be applied to the device as a strip, rather than discrete beads. This may facilitate application on an assembly line by an automated process.

The oral hygiene device described herein can be used to clean teeth and/or freshen the mouth as described above. In some embodiments, the devices can be used as a supplement to a traditional tooth care routine, which generally involves twice daily brushing. For example, the devices can be used on-the-go, in between brushings, as a supplement to improve oral healthcare. In some embodiments, this is facilitated by the fact that the devices can be configured to be useable without requiring access to water and/or a bathroom. In addition, by reducing or eliminating the need for people to find public restrooms while on-the-go to clean their teeth, people can avoid the unsanitary conditions associated with public restrooms (such as the spread of germs and other unsanitary material due to toilet plume).

In some embodiments, the devices can be configured to provide fluoride as means to prevent tooth decay. The Global Burden of Disease Study from 2016 estimated that oral diseases affected half of the world's population (3.58 billion people) with dental caries (tooth decay) in permanent teeth being the most prevalent condition assessed. Poor oral hygiene and inadequate exposure to fluoride can have negative effects on oral health. Further, oral health is a key indicator of overall health, wellbeing and quality of life. The World Health Organization (WHO) defines oral health as "a state of being free from chronic mouth and facial pain, oral and throat cancer, oral infection and sores, periodontal (gum) disease, tooth decay, tooth loss, and other diseases and disorders that limit an individual's capacity in biting, chewing, smiling, speaking, and psychosocial wellbeing."

Additionally, poor oral health can be even more common in developing countries, with increasing urbanization and changes in living conditions. The prevalence of oral diseases continues to increase notably due to inadequate exposure to fluoride and poor access to primary oral health care services. Heavy marketing of sugars, tobacco and alcohol also leads to growing consumption of unhealthy products.

Dental caries results when microbial biofilm (plaque) formed on the tooth surface converts the free sugars contained in foods and drinks into acids that dissolve tooth enamel and dentine over time. With continued high intake of free sugars, inadequate exposure to fluoride and without regular microbial biofilm removal, tooth structures are destroyed, resulting in development of cavities and pain, impacts on oral-health-related quality of life, and, in the advanced stage, tooth loss and systemic infection.

The burden of oral diseases and other non-communicable diseases (NCDs) can be reduced through public health interventions by addressing common risk factors. In addition, to the NCDs' common risk factors, inadequate exposure to fluoride and a number of social determinants of health should be addressed to prevent oral diseases and reduce oral health inequalities.

Dental caries can be largely prevented by maintaining a constant low level of fluoride in the oral cavity. Optimal fluoride can be obtained from different sources such as fluoridated drinking water, salt, milk and toothpaste. Twice-daily tooth brushing with fluoride-containing toothpaste (1000 to 1500 ppm) should be encouraged, although people often fail to use adequate fluoride. Long-term exposure to an optimal level of fluoride results in substantially lower incidence and prevalence of tooth decay across all ages. Accordingly, the devices described herein can be used as a supplement for applying fluoride. This is even more true for developing areas where access to water is not available.

In some embodiments, the devices can be configured to provide a dose of fluoride of approximately 1000-1500 ppm. This dose of fluoride can be included in the device, but would have to be spit out and cannot be swallowed. It may be in the dabs or beads or dispensed in another mode, such as paste coated within the channel of the device. This can greatly improve dental health in areas where access to water is limited. This may be especially helpful for children (especially since an estimated 486 million children suffer from Patient motivation and very detailed instructions are needed for optimal oral hygiene while in braces. This help could come from the practitioner, parent, or the patient. This invention is very easy to understand, simple to use, and can be used anywhere and at any time. This invention will clean the surface area of the teeth, gums, bracket, wire and the bands The large investment in orthodontics lends itself to an inbred motivation for improved oral care that will result in successful braces without unsightly white spots that are many times permanent.

While the above detailed description has shown, described, and pointed out novel features of the development as applied to various embodiments, it will be understood that various omissions, substitutions, and changes in the form and details of the device or process illustrated may be made by those skilled in the art without departing from the spirit of the development. As will be recognized, the present development may be embodied within a form that does not provide all of the features and benefits set forth herein, as some features may be used or practiced separately from others. All changes which come within the meaning and range of equivalency of the claims are to be embraced within their scope.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present development. This development is susceptible to modifications in the methods and materials, as well as alterations in the fabrication methods and equipment. Such modifications will become apparent to those skilled in the art from a consideration of this disclosure or practice of the development disclosed herein. Consequently, it is not intended that this development be limited to the specific embodiments disclosed herein, but that it covers all modifications and alternatives coming within the true scope and spirit of the development.

What is claimed is:

1. An oral hygiene device comprising:
   a U-shaped body comprising a first material, the U-shaped body comprising a channel configured to receive a user's upper or lower teeth;
   one or more teeth cleaning features over molded onto the U-shaped body, the one or more teeth cleaning features made of a second material that is softer than the first material and the one or more teeth cleaning features comprising:
      an outer plurality of ribs disposed within the channel, at least some of the outer plurality of ribs comprising:
         an outer lower portion formed on a bottom wall of the channel between an inner wall and an outer wall, wherein the outer lower portion extends upwardly from the bottom wall; and
         an outer extension portion formed on an inner surface of the outer wall and connected to the outer lower portion, wherein the outer extension portion extends substantially perpendicular with respect to the bottom wall and wherein an outer finger extends from the outer extension portion above the outer wall at an angle of approximately 90 degrees with respect to the outer wall of the channel, wherein the finger is adapted to clean at least one of above or below orthodontia during use;
      an inner plurality of ribs disposed within the channel, at least some of the inner plurality of ribs comprising:
         an inner lower portion formed on the bottom wall of the channel between the inner wall and the outer wall, wherein the inner lower portion extends upwardly from the bottom wall; and
         an inner extension portion formed on an inner surface of the inner wall and connected to the inner lower portion, wherein the inner extension portion extends along a shape of the inner wall and wherein an inner finger extends from the inner extension portion above the inner wall at an angle of approximately 90 or 45 degrees with respect to the inner wall of the channel, wherein the finger is adapted to clean at least one of above or below orthodontia during use, and
      one or more reservoirs holding a dab configured to freshen a user's mouth, wherein the dab is configured to be useable without water;
   wherein the oral hygiene device is configured to be useable without access to water or a restroom.

2. The oral hygiene device of claim 1, wherein the first material comprises polypropylene, and wherein the second material comprises a thermoplastic elastomer (TPE) or a thermoplastic polyurethane (TPU).

3. The oral hygiene device of claim 1, wherein the second material comprises a Shore A hardness between 80 and 90.

4. The oral hygiene device of claim 1, further comprising one or more tongue cleaning features extending from a bottom surface of a bottom wall of the channel of the U-shaped body.

5. The oral hygiene device of claim 4, wherein the one or more tongue cleaning features comprise one or more ridges formed of the second material.

6. The oral hygiene device of claim 1, wherein the reservoirs are configured to extend through the bottom wall of the U-shaped body.

7. The oral hygiene device of claim 6, wherein the reservoirs are configured to extend at least 0.5 mm above and below the bottom wall of the U-shaped body.

8. The oral hygiene device of claim 7, wherein the reservoirs comprise openings extending therethrough to facilitate release of the dab.

9. The oral hygiene device of claim 1, wherein the dab comprises a formulation that is safe to swallow.

10. The oral hygiene device of claim 1, wherein the dab comprises fluoride.

11. The oral hygiene device of claim 1, wherein the one or more teeth cleaning features are configured to contact at least 50%, at least 60%, at least 75%, at least 80%, or at least 90% of the user's upper or lower teeth simultaneously.

12. The oral hygiene device of claim 1, further comprising a handle extending from the U-shaped body.

13. A method for freshening or cleaning a user having orthodontia's mouth, the method comprising:
   inserting an oral hygiene device into a user's mouth, the oral hygiene device comprising:
      a U-shaped body comprising a first material, the U-shaped body comprising a channel configured to receive a user's upper or lower teeth, the channel comprising an inner wall, a bottom wall, and an outer wall, wherein the inner wall and the outward wall extend from the bottom wall to form the channel;
      teeth cleaning features over molded onto the U-shaped body, the teeth cleaning features made of a second material that is softer than the first material and the teeth cleaning features comprising:

an outer plurality of ribs disposed within the channel, at least some of the outer plurality of ribs comprising:
- an outer lower portion formed on a bottom wall of the channel between an inner wall and an outer wall, wherein the outer lower portion extends upwardly from the bottom wall; and
- an outer extension portion formed on an inner surface of the outer wall and connected to the outer lower portion, wherein the outer extension portion extends substantially perpendicular with respect to the bottom wall and wherein an outer finger extends from the outer extension portion above the outer wall at an angle of approximately 90 degrees with respect to the outer wall of the channel, wherein the finger is adapted to clean at least one of above or below orthodontia during use;

an inner plurality of ribs disposed within the channel, at least some of the inner plurality of ribs comprising:
- an inner lower portion formed on the bottom wall of the channel between the inner wall and the outer wall, wherein the inner lower portion extends upwardly from the bottom wall; and
- an inner extension portion formed on an inner surface of the inner wall and connected to the inner lower portion, wherein the inner extension portion extends along a shape of the inner wall and wherein an inner finger extends from the inner extension portion above the inner wall at an angle of approximately 90 or 45 degrees with respect to the inner wall of the channel, wherein the finger is adapted to clean at least one of above or below orthodontia during use, wherein the outer and inner fingers are configured in size and shape to contact at least a portion of an outer and inner gumline during use of the oral hygiene device;

one or more reservoirs holding a dab configured to freshen the user's mouth, wherein the dab is configured to be useable without water;

wherein the oral hygiene device is configured to be useable without access to water or a restroom; and positioning the oral hygiene device such that the user's upper or lower teeth and associated orthodontia are positioned within the channel;

moving the oral hygiene device side to side and front to back to clean the user's upper or lower teeth, wherein moving the oral hygiene device distributes a formulation from the dab in the one or more reservoirs of the oral hygiene device and causes at least one of the outer or inner fingers to clean at least one of above or below a bracket of the user's orthodontia;

flipping the oral hygiene device such that the other of the user's upper or lower teeth are positioned within the channel; and moving the oral hygiene device side to side and front to back to clean the other of the user's upper or lower teeth and associated orthodontia.

14. The method of claim 13, wherein the method is performed without access to water or a restroom.

15. The method of claim 13, further comprising cleaning the user's tongue with one or more tongue cleaning features of the oral hygiene device by running the one or more tongue cleaning features of the oral hygiene device over the tongue.

16. The method of claim 13, wherein the oral hygiene device is configured to contact at least 50%, at least 60%, at least 75%, at least 80%, or at least 90% of the user's upper or lower teeth simultaneously.

17. The method of claim 13, further comprising disposing of the oral hygiene device after use.

18. The method of claim 13, further comprising swallowing the formulation, and wherein the formulation is safe to swallow.

19. The method of claim 13, wherein the formulation comprises fluoride.

* * * * *